(12) United States Patent
Lehto

(10) Patent No.: US 8,168,134 B2
(45) Date of Patent: May 1, 2012

(54) BIOLOGICAL ANALYSIS SYSTEMS, DEVICES AND METHODS

(75) Inventor: Dennis Lehto, Santa Clara, CA (US)

(73) Assignee: Life Technologies Corporation, Carlsbad, CA (US)

( * ) Notice: Subject to any disclaimer, the term of this patent is extended or adjusted under 35 U.S.C. 154(b) by 125 days.

(21) Appl. No.: 12/646,787

(22) Filed: Dec. 23, 2009

(65) Prior Publication Data

US 2010/0166612 A1   Jul. 1, 2010

Related U.S. Application Data

(60) Provisional application No. 61/140,836, filed on Dec. 24, 2008.

(51) Int. Cl.
*G01N 31/22* (2006.01)
(52) U.S. Cl. ........................................ 422/407
(58) Field of Classification Search ............ 422/407
See application file for complete search history.

(56) References Cited

U.S. PATENT DOCUMENTS

| 4,207,394 A * | 6/1980 | Aldridge et al. ............... 435/34 |
| 6,654,505 B2 | 11/2003 | Bridgham et al. |
| 7,189,359 B2 | 3/2007 | Yuan et al. |
| 7,439,014 B2 | 10/2008 | Pamula et al. |
| 2005/0042149 A1 * | 2/2005 | Bard ............................. 422/130 |

FOREIGN PATENT DOCUMENTS

WO   WO-2010/075568   7/2010

OTHER PUBLICATIONS

PCT/US2009/069502 International Search Report/Written Opinion mailed on Aug. 19, 2010.

* cited by examiner

*Primary Examiner* — Bobby Ramdhanie

(57) ABSTRACT

A device for performing biological sample reactions comprising a plurality of flow cells each with at least one port for receiving reaction fluids delivered to a chamber of each flow cell and a manifold configured to receive the plurality of flow cells, wherein the manifold is configured to receive at least one reaction fluid, and wherein each flow cell is configured with a sample holder wherein the sample holder contains biological sample.

12 Claims, 14 Drawing Sheets

BIOLOGICAL ANALYSIS SYSTEMS, DEVICES AND METHODS

The present application claims the benefit of priority under 35 U.S.C. 119 to U.S. Provisional Application No. 61/140,836, filed Dec. 24, 2008, incorporated herein by reference.

TECHNICAL FIELD

The present teachings pertain generally to devices, systems, and methods for performing biological and/or biochemical reactions and/or analyses. More particularly, the present teachings are directed to various instruments useful in performing large scale parallel reactions on solid phase supports, such as, for example, performing sequencing by synthesis on beaded microarrays.

INTRODUCTION

The section headings used herein are for organizational purposes only and are not to be construed as limiting the subject matter described in any way.

Increasing efficiency and throughput are significant considerations in the development of tools and techniques for performing various aspects of biological and/or biochemical analysis. In the field of genomic sequencing, for example, various approaches have evolved in an attempt to obtain faster and less costly techniques that can be applied to perform sequencing for research applications and/or on an individualized basis. One approach to such sequencing uses microarrays having a plurality of small (e.g., from 1 micron to several hundred microns) analysis sites or beads arranged on a surface of a support. Depending on the particular technique used, one or more single nucleic acid strands of interest (e.g., template nucleic acids strands) are attached to the analysis site or bead. Bases are added either by polymerase to a complementary primer sequence to the template or by recognition of ligase as a match, and the sequence of the template strand is revealed. Typically some sort of optical signal, such as, for example, fluorescence, is detected, for example by a microscope, to determine the sequence in these techniques. The analysis sites of the microarrays can be in the form of small solid elements (e.g., beads) on each of which numerous identical oligonucleotides can be synthesized, with the solid elements being in turn placed on a support (e.g., substrate surface). Alternatively, the analysis sites can be sites directly on the substrate surface itself.

To perform sequencing, the microarrays of template nucleic acid strands to be synthesized can be loaded into a flow cell chamber mounted on a stage (for example a microscope stage) and a mixture of sample, reagents and/or buffers can be introduced into the chamber to react with the microarrays. Massively parallel sequencing of the same or differing templates can occur using the microarray format due to the ability to place large numbers (e.g., millions) of template strands on a substrate, which can be in the form of a generally planar substrate or slide, for example a glass or polymer substrate or microscope slide. Reactions occurring between the microarray templates and the loaded sample, reagents, and/or buffers within the flow cell can be analyzed using conventional fluorescence detection and microscopy techniques with which those having skill in the art are familiar.

In some configurations, flow cells can include a reaction chamber in which a sample holder, such as, for example, a microarrayed or bead-supporting microscope slide or similar substrate with nucleic acid templates bound, attached, or residing in proximity thereto, is configured to be seated and held in position. The reaction chamber can be defined between a sample holder (e.g., a substrate, such as, for example, a microscope slide, holding a sample) and a heater block configured to transfer heat to the chamber from various temperature control and heat exchange mechanisms (e.g., Peltier devices, cooling components, heat sinks, and/or feedback controllers, etc.) external to the chamber. A body on which the block is supported can be configured to move relative to a stage and/or other frame to place the flow cell in a position for performing reactions in the reaction chamber and imaging the reaction chamber. One or more sealing members, such as, for example, O-rings, gaskets, or the like, can be provided, for example, on the surface of the block that faces the reaction chamber and can be configured to surround at least a portion of the sample holder to provide sealing of the portion of the sample holder within the chamber and where the reactions occur. Such gaskets can be configured to engage an outer region of a surface of a microarray substrate to define the outer perimeter of the area of the substrate at which reactions can take place. In such configurations, the reaction chamber (e.g., the chamber into which substances are introduced to the flow cell) is defined between the heater block and the substrate, with the sealing mechanism on the heater block forming a seal to seal the chamber. Various inlet and outlet ports can be provided on the flow cell to permit the flow of desired substances (e.g., samples, reagents, lysis chemicals, and/or buffers, etc.) into and out of the reaction chamber and into reactive contact with the microarray and the templates thereon.

In some cases, it can be awkward for a user to mount the substrate vertically within a flow cell. Moreover, when initially mounting the substrate in a vertical position, substance (e.g., liquid) on the substrate can run off the substrate and onto other components (e.g., the microscope stage) due to the open position of the flow cell during initial loading of the substrate. In addition, once mounted vertically, the side of the substrate that faces the stage is not accessible and thus any contamination or drips can not be wiped off, which can affect detection and analysis. It can be desirable, therefore, to provide a dual door flow cell arrangement in which the substrate can be mounted horizontally by a user (e.g., with the larger surface area surface of the substrate substantially parallel to the ground) and from that mounted position, moved to a substantially vertical orientation (e.g., with the larger surface area of the substrate substantially parallel to the ground) upon closing the flow cell chamber to commence reactions therein.

Additionally, the flow cell can include one or more optically transparent regions such that the sample holder, and in particular the reactions occurring between the sample held by the sample holder and the substances introduced into the flow cell reaction chamber, can be detected and observed via mechanisms located external to the flow cell (e.g., various optics, microscope components and/or optical fluorescent detectors). In some configurations, the surface of a microarray substrate that faces the chamber and where the reactions take place faces in a direction opposite to where the optics used for analysis and detection are positioned.

Flow cells can be mounted on a stage that can translate in three dimensions, and can be oriented either in a horizontal or vertical position, with the optics, light sources, and/or imaging devices being positioned appropriately relative thereto.

Conventional flow cell systems used for sequencing-by-synthesis and/or other biological analysis applications can permit a reduction in the amount of reagents, sample, and/or buffers needed for reactions and/or analysis and relatively high throughput for sequencing Nonetheless, it can be desirable to improve such systems to help achieve more efficient biological analysis (e.g., sequencing).

For example, it can be desirable to modify conventional flow cell systems to increase throughput of sample analysis. It also can be desirable to modify conventional flow cell systems to improve reagent use, recycling of reagents and the movement of reagents by electrowetting process. It can further be desirable to improve thermal features of conventional flow cell systems. In addition, it can be desirable to improve on the efficiency with which microarrayed substrates or other sample holders can be transported and mounted to flow cell systems for analysis (e.g., sequencing).

SUMMARY OF EXEMPLARY EMBODIMENTS

The present invention can satisfy one or more of the above-mentioned desirable features. Other features and/or advantages can become apparent from the description which follows.

According to various embodiments, the invention comprises a device for performing biological sample reactions, the device further comprising: a plurality of flow cells comprising at least one port in each flow cell for receiving reaction fluids delivered to a chamber of each flow cell; and a manifold configured to receive the plurality of flow cells, wherein the manifold is configured to receive at least one reaction fluid, and wherein each flow cell is configured with a sample holder wherein the sample holder contains biological sample.

In other embodiments, the invention comprises a device for performing biological sample reactions, the device further comprising a plurality of independently positionable flow cells; each flow cell further comprising at least two channels comprising an entry port and an exit port wherein at least one reaction fluid is introduced into said flow cells through the entry port and leaves said flow cells through the exit port.

It still other embodiments, the invention comprises a device for performing biological sample reactions, the device further comprising a flow cell configured with at least one integrated funnel for directing fluids into the flow cell through an entry port wherein the funnel has a larger diameter than the entry port.

In still further embodiments, the invention comprises a device for performing biological sample reactions, the device further comprising: a plurality of independently moveable flow cells comprising at least one port in each flow cell for receiving reaction fluids delivered to a chamber of each flow cell, each flow cell further comprising an at least partially transparent portion through which selected optical signals can be transmitted; an optical system configured to detect optical signals transmitted through the at least partially transparent portion of the flow cell; and at least one biological sample contained within the chamber of the flow cell which transmits an optical signal detectable by the optical system.

According to various embodiments, the present teachings include a device for performing biological sample reactions can include a plurality of flow cells having at least one port system in each flow cell for receiving reaction fluids within a chamber of each flow cell; a manifold configured to receive the plurality of flow cells, wherein the manifold is configured to receive at least one reaction fluid, and wherein each flow cell is configured to receive a sample holder, wherein each sample holder contains biological sample; and wherein the reaction fluids are recycled.

In various exemplary embodiments, the present teachings include movement of reaction fluids by electrowetting processes within the manifold. The manifold can reside adjacent a plurality of heater blocks and the electrical field of the manifold and the plurality of heater blocks are configured to be independently controlled.

In accordance with yet other exemplary embodiments, the present teachings can include a flow cell having a first substrate and a second substrate, wherein said second substrate is laminated to said first substrate to form a laminated substrate flow cell reaction chamber with said laminated substrate further having at least two channels, each channel having a port for the induction or aspiration of reaction fluids into the flow cell reaction chamber. The laminated substrate can also contain biological sample.

In another exemplary embodiment, the present teachings can include device for performing biological sample reactions, the device having: a plurality of flow cell cartridges configured with at least one funnel port at one end of the flow cell and a second port located at the opposite end of the flow cell. The funnel port can have an internal ledge further having a waste port opening, wherein said waste port opening is elevated above the funnel port opening, wherein said funnel port opening is in direct communication with said flow cell cartridge and said waste port is connected to a waste receptacle. In various embodiments, the funnel port has a diameter larger than that of an entry port into the flow cell and may be used to facilitate addition of reagents to the flow cell. The funnel shape and size may also be configured to contain a specified quantity or volume of reagent to be dispensed into the flow cell. The device can further have a syringe pump, wherein a reagent is aspirated by the pump into the funnel port and then into the flow cell, said reagent level in said funnel port remaining below the level of the waste port. The reagent can be recycled between biological reactions occurring within the flow cell.

In accordance with yet other exemplary embodiments, the present teachings can include a device for performing biological sample reactions, the device having a plurality of flow cells having a first surface and a second surface wherein said first and second surfaces are configured to define a flow cell reaction chamber wherein said first surface has at least one biological sample such as a microarray of nucleic acids for performing nucleic acid sequencing.

Additional objects and advantages of the invention will be set forth in part in the description which follows, and in part will be obvious from the description, or can be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive.

The accompanying drawings, which are incorporated in and constitute a part of this specification, illustrate some exemplary embodiments and, together with the description, serve to explain the principles.

BRIEF DESCRIPTION OF THE DRAWINGS

The skilled artisan will understand that the drawings, described below, are for illustration purposes only. The drawings are not intended to limit the scope of the present teachings in any way

DESCRIPTION OF EXEMPLARY EMBODIMENTS

Figure 1:
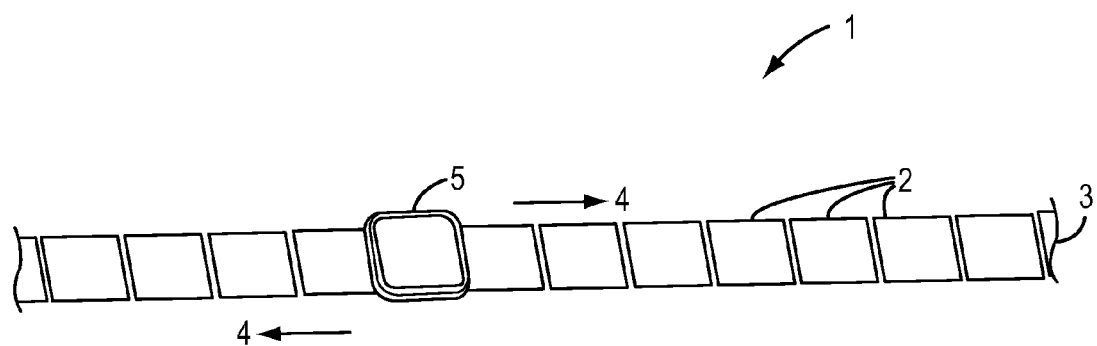
FIG. 1 illustrates movement of an aqueous fluid in response an electrical field in accordance with the present teachings.

The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

Throughout the specification, reference is made to biological sample and/or biological samples. It should be understood that the biological analysis instruments in accordance with the present teachings may be configured to perform processes on multiple amounts of sample simultaneously. Further, differing types of sample can be processed simultaneously. Thus, when reference is made to a biological sample being provided in a reaction chamber, it should be understood that the term can refer to either a single type of sample in a single amount, multiple amounts of a single type of sample, and/or multiple amounts of differing types of sample. The term also can be used to refer to a bulk amount of substance placed in the reaction chamber. Further, the term sample can include the various reagents, etc. that are introduced to the chamber to perform an analysis or other process therein.

In various exemplary embodiments described herein, the flow cells can be configured to flow reagents into the reaction chambers to react with microarrays of template nucleic acid in order to perform sequencing of the template nucleic acid residing on the substrate or bead. Examples of various substrates holding nucleic acid templates and methods of making such substrates can be found in WO 2006/084132, which published Aug. 10, 2006, entitled "REAGENTS, METHODS, AND LIBRARIES FOR BEAD-BASED SEQUENCING," and is incorporated herein by reference in its entirety.

The term "nucleic acid" can be used interchangeably with "polynucleotide" or "oligonucleotide" and can include single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, H+, NH4+, trialkylammonium, Mg2+, Na+ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleosides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5' terminus, 3' terminus, a nucleobase, an internucleotide linkage, a sugar, amino, sulfide, hydroxyl, or carboxyl. See, for example, U.S. Pat. No. 6,316,610 B2, which issued Nov. 13, 2001 and is entitled "LABELLED OLIGONUCLEOTIDES SYNTHESIZED ON SOLID SUPPORTS," which is incorporated herein by reference. Similarly, other modifications can be made at the indicated sites as deemed appropriate.

The term "reagent" should be understood to mean any reaction component that in any way affects how a desired reaction can proceed or be analyzed. The reagent can comprise a reactive or non-reactive component. It is not necessary for the reagent to participate in the reaction. The reagent can be a recoverable component comprising for example, a solvent and/or a catalyst. The reagent can comprise a promoter, accelerant, or retardant that is not necessary for a reaction but affects the reaction, for example, affects the rate of the reaction. A reagent can comprise, for example, one member of a binding pair, a buffer, or a DNA that hybridizes to another DNA. The term "reagent" is used synonymous with the term "reaction component."

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

Reference will now be made in detail to various exemplary embodiments of the present teachings, examples of which are illustrated in the accompanying drawings. Wherever possible, the same reference numbers will be used throughout the drawings to refer to the same or like parts.

Flow cells in accordance with exemplary embodiments of the present teachings can have a variety of forms and configurations. In general, a flow cell can include any structure configured to define a reaction chamber to receive a biological sample for analysis and various flow control structures and mechanisms to permit sample, reagents, buffers and/or other substances from a source external introduced into the flow cell reaction chamber to react with the biological sample (e.g., template nucleic acids when performing sequencing) contained in the reaction chamber. In various exemplary configurations, flow cells can also include or be associated with various thermal components configured to heat and/or cool the reaction chamber. Also, various exemplary flow cell configurations can have optically transparent portions that permit imaging and/or other detection of the reaction chamber, for example, to perform analysis of various reactions that can be performed in the reaction chamber. Those having skill in the art are familiar with various flow cell configurations. For further details regarding flow cell arrangements, reference can be made to WO 2006/084132, U.S. Pat. Nos. 6,406,848 and 6,654,505, U.S. patent application Ser. No. 12/244,701 and PCT Publication No. WO 98/05330, which are incorporated by reference herein.

To increase throughput during biological reactions and analysis, in one exemplary embodiment a manifold flow cell system incorporating electrowetting to move aqueous fluids into one or more flow cells is described and includes at least two segregated reaction chambers such that processing (e.g., reactions) can occur separately within each formed chamber. For example, different reagents can move into each reaction chamber in response to an electric field within the manifold. Exemplary embodiments of such a system using electrowetting to direct fluid flow direction are described in U.S. Pat. No. 7,439,014, issued Oct. 21, 2008 and entitled "Droplet-Based Surface Modification and Washing", which is incorporated by reference in its entirety herein.

Figure 2:
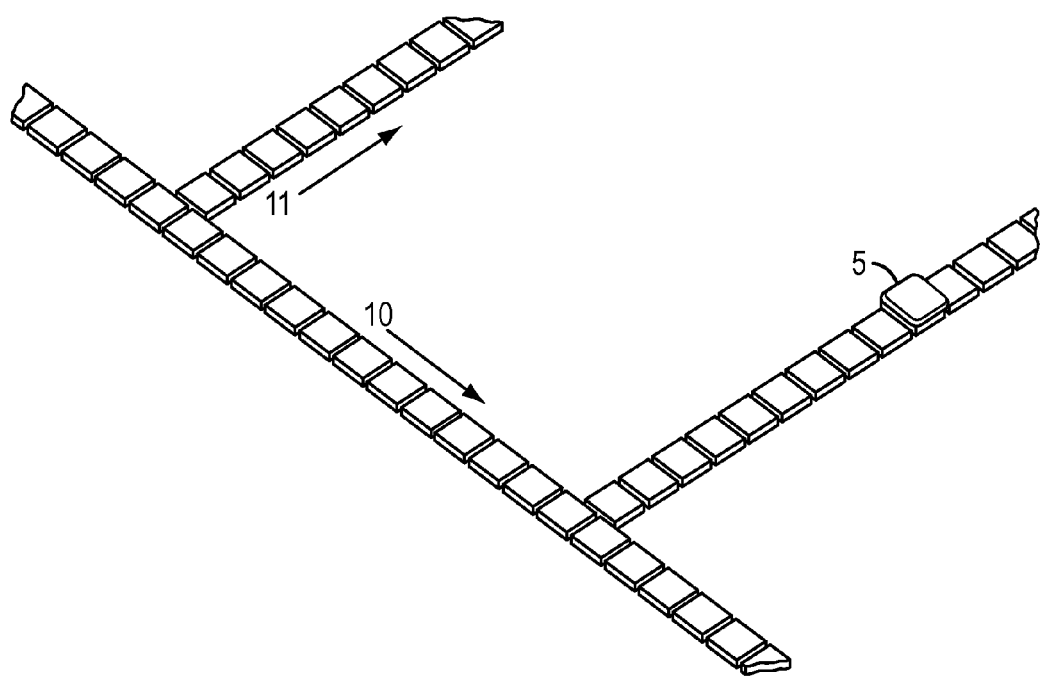
FIG. 2 illustrates movement of an aqueous fluid in both an X- and Y-axis in response to an electrical field in accordance with the present teachings.
Figure 3:
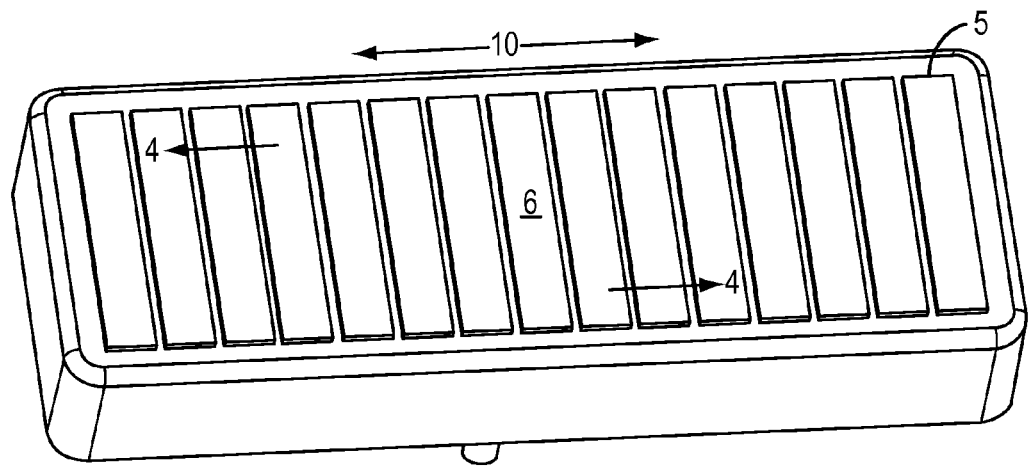
FIG. 3 illustrates movement of an aqueous fluid in bulk in response an electrical field in accordance with the present teachings.

With reference to FIG. 1, application of an electrical field 1 utilizing, as an example, successive electrical field 2 changes along a defined grid or pathway 3 directionally directs the flow 4 of liquid or water-based reagent 5 in response to an applied electrical field. FIG. 2 further illustrates that electrowetting can also change the direction of flow of a reagent 5 in relation to both the X-10 and Y-11 axis. The liquied or water-based reagent 5 can move in either a drop-wise fashion or as a quantity of reagent within the reaction chamber of the flow cell. As illustrated in FIG. 3, a bulk quantity of a reagent 5 within a reaction chamber 6 can migrate directionally 4 in response to an electric field in an X-axis 10. Conversely, the bulk reagent 5 can also be returned to the starting position within chamber 6. Also envisioned is bulk reagent migration in a Y-axis as would be understood by one of skill in the art.

Figure 4:
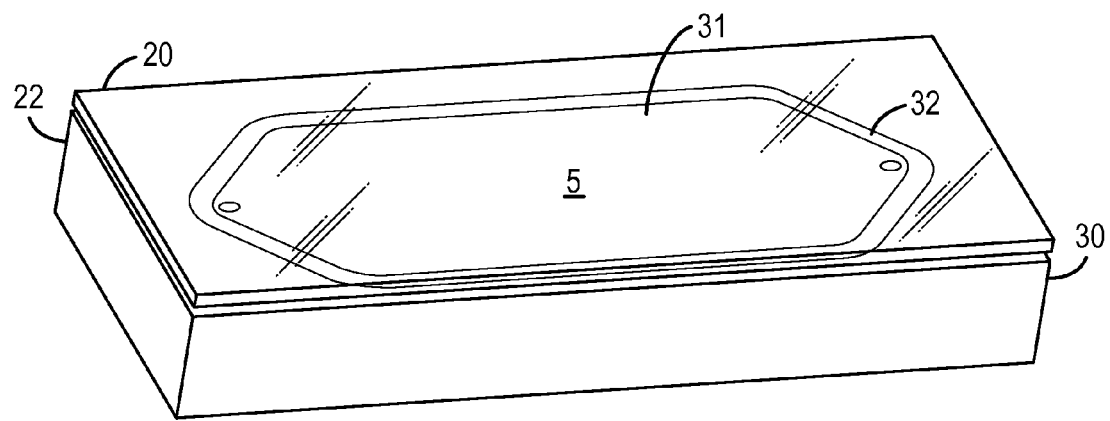
FIG. 4 is a perspective view of an exemplary embodiment of movement of an aqueous fluid in bulk in response to two independently applied electrical fields in accordance with the present teachings.

FIG. 4 illustrates reagent 5 in bulk quantity within a chamber 30 formed by clamping (not shown) a substrate 20 on top of a heater block 22. The electrical field can be incorporated into the surface of the heater block 22, for example, or in the substrate, for example, a glass slide. A first electrical field 31 surrounded by a second electrical filed 32 is within chamber 30. Furthermore, a reagent 5 can be withdrawn from the field 31 of the chamber by application of a separate electrical field 32 located at the perimeter of chamber 30. As can be appreciated by the skilled artisan, such liquied or water-based reagent movement offers the advantages of reagent conservation, rapid reagent cycling (as in sequencing by ligation methodologies), a way to manage reagent volume usage as well as a decrease in reagent volume used in conjunction with a reduce chamber 30 volume. The reagent can move through the chamber 30 in response to an electric field applied by a variety of mechanisms including e.g., electrowetting, an electric field, an electrode and/or dielectrophoresis, and so on.

Figure 5:
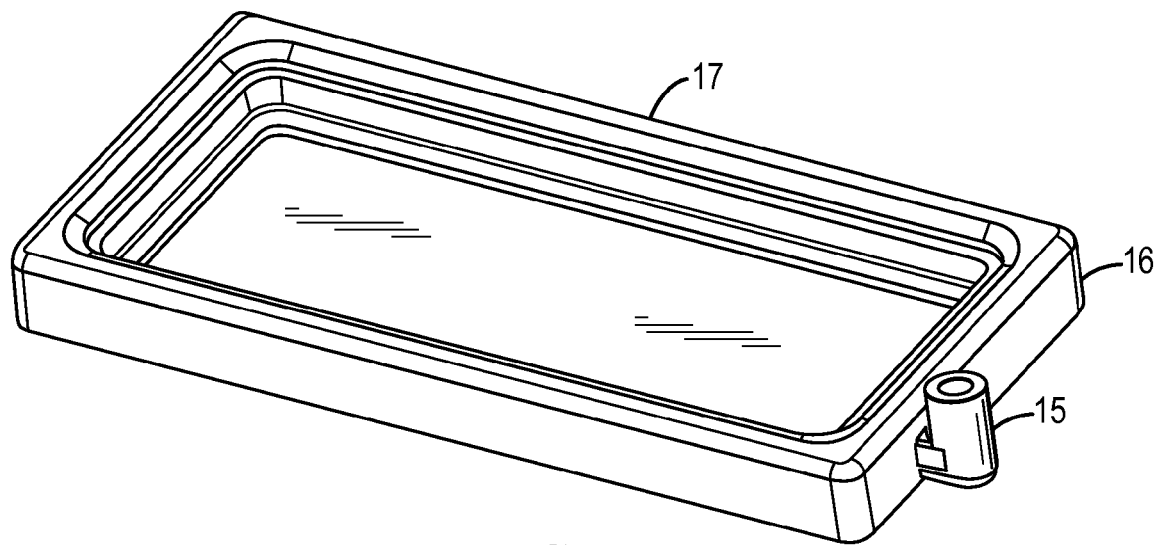
FIG. 5 is a perspective view of an exemplary embodiment of a molded frame containing a flow cell reaction chamber mated to a waste port in accordance with the present teachings.

FIG. 5 illustrates an exemplary method of introducing a reagent into a flow cell via a funnel 15. Funnel 15 is connected to the chamber (not shown) through a port connecting the chamber and the funnel 15 which spans across frame 16 of slide carrier 17. In various embodiments, the funnel 15 has a diameter larger than that of the entry port into the flow cell and may be used to facilitate addition of reagents to the flow cell. The funnel shape and size may also be configured to contain a specified quantity or volume of reagent to be dispensed into the flow cell. Those ordinarily skilled in the art would understand various apparatus and structures containing reagent (e.g., pipettes, vacuums, robots, and associated valves and/or pumps, etc.) that can be used to introduce and extract reagents into the reaction chambers of the flow cells described herein; details regarding such reagent induction and extraction mechanisms therefore are not provided.

Although various exemplary embodiments shown and described herein describe the use of a substrate that supports a microarray of nucleic acid templates (for example on beads or secured to the substrate) as the sample holder introduced into the flow cell reaction chambers, it is considered within the scope of the present teachings that the flow cell reaction chambers set forth herein are configured to hold one or more biological samples for analysis that can be provided in a variety of differing types of sample holders, which can be supported by sample blocks of the flow cells. By way of example, the flow cells can be configured to receive sample holders including, for example, recesses and/or wells in a microtiter plate, capillaries, tubes/microtubes, microfluidic devices/chambers, throughhole plates, sample trays, and other types of sample holders. Sample holders can also comprise various materials having locations for holding or retaining samples such as on a microcard or sample substrate including for example glass, plastic, polymer, metal, or combinations thereof. A substrate can be configured in numerous manners, for example, as a generally planar substrate, such as a microscope slide or planar array, configured to hold an array of templates or other samples, and/or other conventional sample holders used for biological analysis processes in the form of microtiter plates, capillaries, and/or other sample holders configured to be filled with one or more biological samples and which can be supported by the sample blocks in the flow cells. Further, it also is envisioned that one or more biological samples can be introduced directly into the reaction chamber of the flow cell without being held by a substrate, microtiter plate, capillary and/or other sample holder. In one exemplary embodiment of an arrangement wherein the sample is introduced into the reaction chamber without a sample holder, the sample block can also be removed and the reaction chamber itself formed by the flow cell structure being heated and cooled.

Figure 6A:
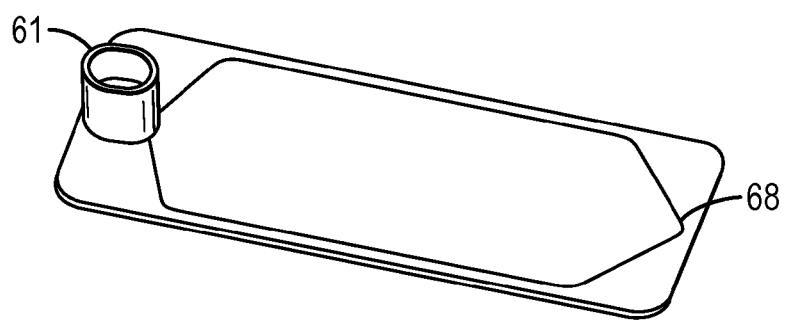
FIG. 6A is a perspective view of an exemplary embodiment of a reagent entry port interconnected to a flow cell reaction chamber in accordance with the present teachings.
Figure 6B:
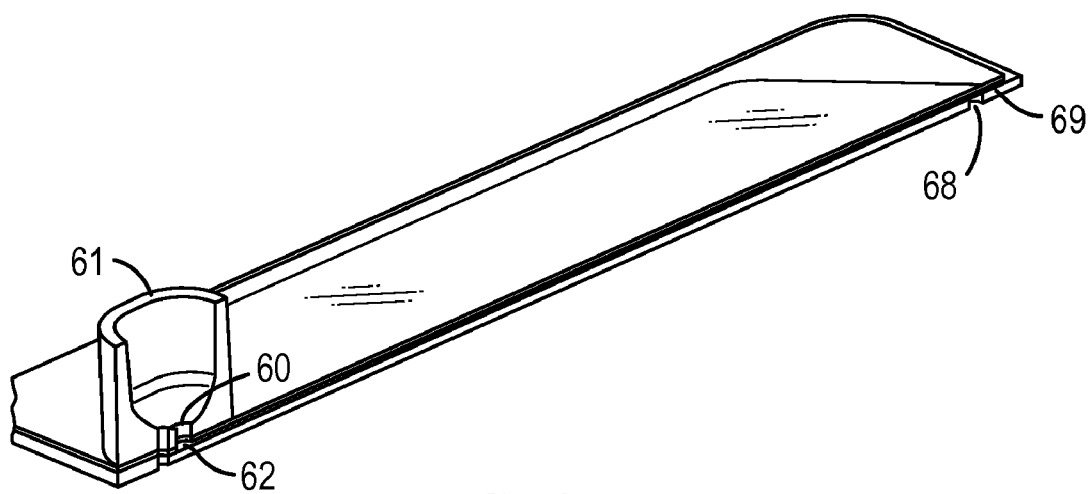
FIG. 6B is a close-up partial sectional view of the exemplary embodiment of FIG. 6A.
Figure 6C:
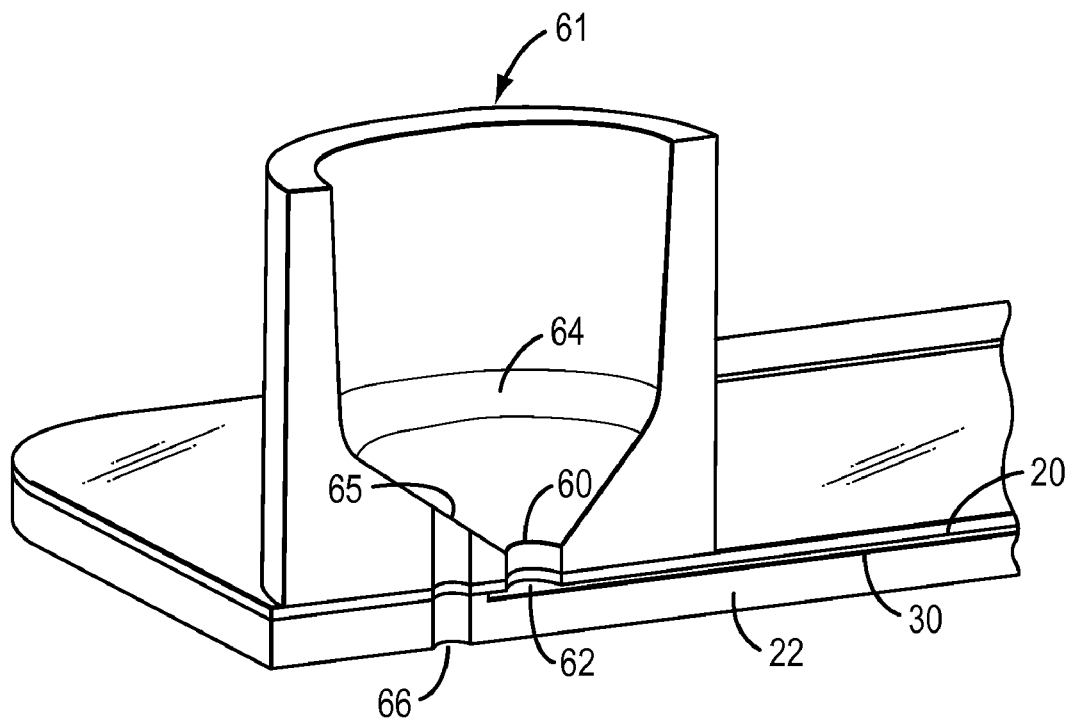
FIG. 6C is a magnified close-up sectional view of the exemplary embodiment of FIG. 6B.

FIG. 6A illustrates another embodiment for the introduction and removal of reagents within a chamber 30 of a flow cell. The overview in FIG. 6A illustrates a reagent entry port 60 (not shown) within a funnel 61 and at the opposite end of chamber 30 a wash/aspirate port 68. As seen in the expand and cut-away view in FIG. 6B at the base of funnel 61 reagent entry port 60 opens 62 into chamber 30 to permit reagent to enter chamber 30 and port 69 opens from chamber 30 to an exit port 68 allowing reagent to exit chamber 30. A further expanded view of port 60 as seen in FIG. 6C illustrates a ledge 64 within the interior circumference of funnel 61 for direction of reagent, e.g., wash buffer, into a second port 65 leading to a waste port 66 posterior port 65. Also visible is the formation of chamber 30 by the mating of substrate 20 to heater block 22. Those of ordinary skill in the art would comprehend various embodiments in which reagents would be introduced into chamber 30 and the subsequent washing of chamber 30 as, for example between sequencing reactions, would be practiced; details regarding such reactions and the reagents involved are not provided.

In various exemplary embodiments, the substrate can be held in a carrier that is configured to be removably engaged with the heater block (also referred to as sample blocks) of the flow cell, which will be described below in more detail with reference to the exemplary embodiments of FIGS. 7-13. The openings of each frame 810 substantially aligns with an optically transparent region of a stage to permit imaging of the substrates loaded in the flow cells.

An issue that can arise in designing such a removable carrier for a flow cell arrangement is how to ensure that the substrate is positioned appropriately within the flow cell reaction chamber such that correct focusing of the optics and detection mechanism occurs. In other words, consistent, precision positioning of the distance between the large surface area of the substrate and the various optics and detection elements should be maintained relatively precisely for each reaction run of the flow cell in order to achieve accurate analyses and detection.

FIGS. 7 and 8A-D: Note, FIG. 7A, charge/aspect ratio The carrier can define an optically transparent region, such as, for example, openings. In various exemplary embodiments, the openings can be covered with a transparent material, such as, for example a glass or plastic material or other suitable transparent composition. The optically transparent regions are configured to substantially align with optical detection and/or imaging of the flow cell reaction chamber and the substrates therein. Various optical detection and imaging systems can be used and can be positioned external to the carrier to detect and gather, for example, in real-time, images of reactions and samples in the reaction chambers through the openings. For details regarding an exemplary detection and imaging system that can be used in conjunction with the carriers described herein, reference is made to WO 2006/081432, incorporated by reference in its entirety herein.

As described below in an exemplary embodiment, retaining clips or other securement mechanisms can be provided to mount a microarray substrate or other carrier. For example, suitable securement mechanisms can comprise small plastic tabs configured to slide sideways to engage the top of the substrate to prevent the substrate from tipping over.

Figure 7A:
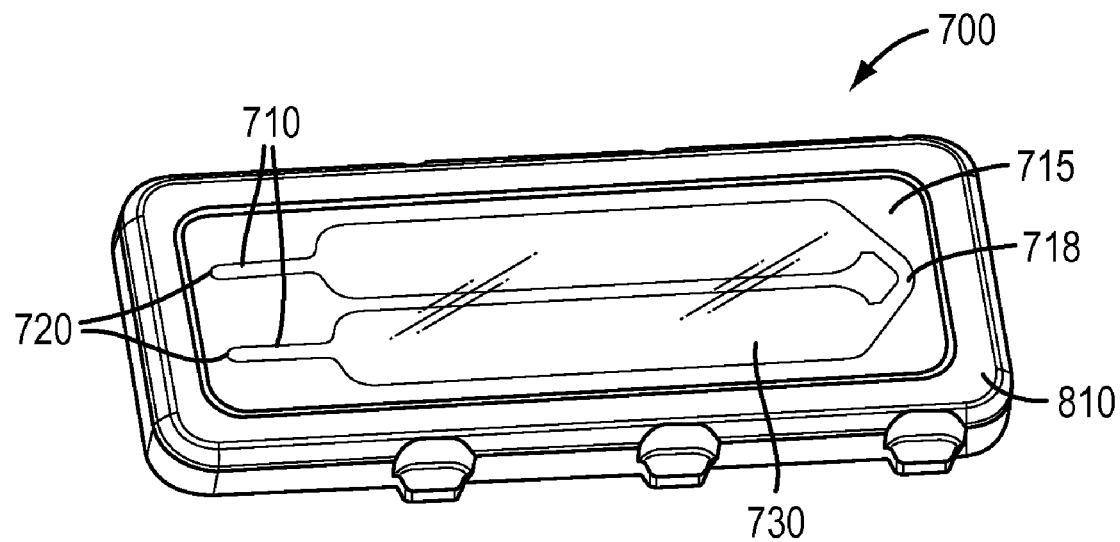
FIG. 7A is a perspective view of an exemplary embodiment of a laminated flow cell mounted within a detachable carrier in accordance with the present teachings.
Figure 7B:
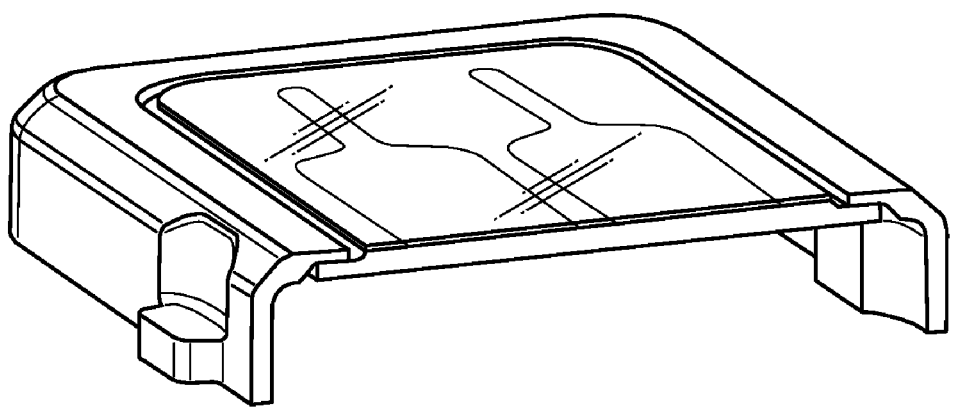
FIG. 7B is a close-up partial sectional view of the exemplary embodiment FIG. 7A.

In one embodiment, a laminated flow cell cartridge 700 can be used as shown in FIG. 7A. Cartridge 700 has a frame 810 for holding a chamber (not shown). Reagents enter and exit the chamber and reactions occur within the chamber. The chamber can be formed by laminating two materials together (for example two glass slides, two glass coverslips, a polymer to glass). To create a sealed reaction flow cell chamber, a silicon rubber gasket can be placed around the perimeter of the two laminated surfaces. Suitable polymers include cyclic olefin polymer (COP) and polymers giving low background and materials which do not fluoresce or generate undesirable optical signals as would be known to one of ordinary skill in the art. The materials selected can permit control of the inner gap of the chamber, keep the surfaces flat and enhance stability of the surfaces. Reagent flow through can be configured to flow through narrow channels 710 to allow control of air bubbles, separation between reagents with air spacers as well as allowing entry and exit ports 720 at a single end of the flow cell.

Additional considerations include the aspect ration between the substrates which form the flow cell reaction chamber, rigidity of the substrates, thermal expansion when two different materials are laminated together and surface properties of the substrates including charge, need for surface preparation, hydrophobicity and/or hydropholicity. When laminating a polymer to glass the adhesive used can have flexibility.

The flow cell of FIG. 7A illustrates a flow cell chamber 30 formed by laminating two substrate surfaces. A pattern 715 is laminated to a substrate to form a "patterned" substrate 730. The "patterned" substrate 730 can have at least two ports 720 for introducing and/or removing reagent into/from the chamber as well as a hydrophobic or hydrophilic surface to facilitate reagent movement. The reagent flow can be in a serpentine fashion through a "joined region" 718 or multiple chambers may be present within the same substrate that are connected or independent of one another.

The chamber of the flow cell can be formed by an almost infinite variety of materials employing a number of differing methods. Exemplary flow cells, both with and without the movement of reagents by means of an electrical charge differential are disclosed herewith. Operation and additional details regarding the reaction chamber of the flow cell are described below.

Aside from providing a flow cell arrangement in which a sample substrate can be loaded in a horizontal position, it can be desirable to minimize direct handling of the substrate by a user loading the substrate and/or transporting the substrate from one workstation to a flow cell for performing reactions and/or analysis of the sample substrate. It also can be desirable to minimize contact between clamping equipment and the substrate when mounting the sample substrate in a flow cell.

To achieve at least some of these desirable features, in various exemplary embodiments, a slide carrier can be configured to hold the sample substrate during loading of the flow cell and within the flow cell while reactions and/or analysis of the substrate is performed. FIGS. 7A-7B, 8A-8D depict various views of some exemplary embodiments of a slide carrier and how that carrier can be configured to be coupled to a frame and sample block of a flow cell configured for enabling loading of a substrate in a horizontal position (such as, for example, the flow cells 1400A, 1400B, 1400C, 1400D 1500A, 1500B, 1500C, 1500D, 1600A, 1600B, 1600C and 1600D, described below).

Reference is now made to exemplary embodiments in FIGS. 8A to 8D to assembly of the components of a slide carrier.

Figure 8A:
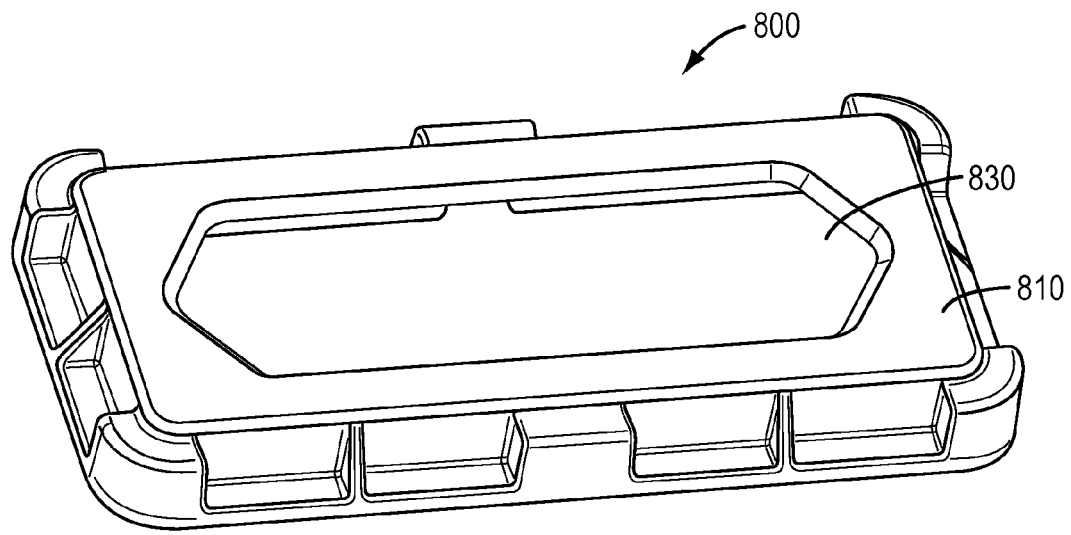
FIG. 8A is a perspective view of an exemplary embodiment of a detachable flow cell carrier in accordance with the present teachings.
Figure 8B:
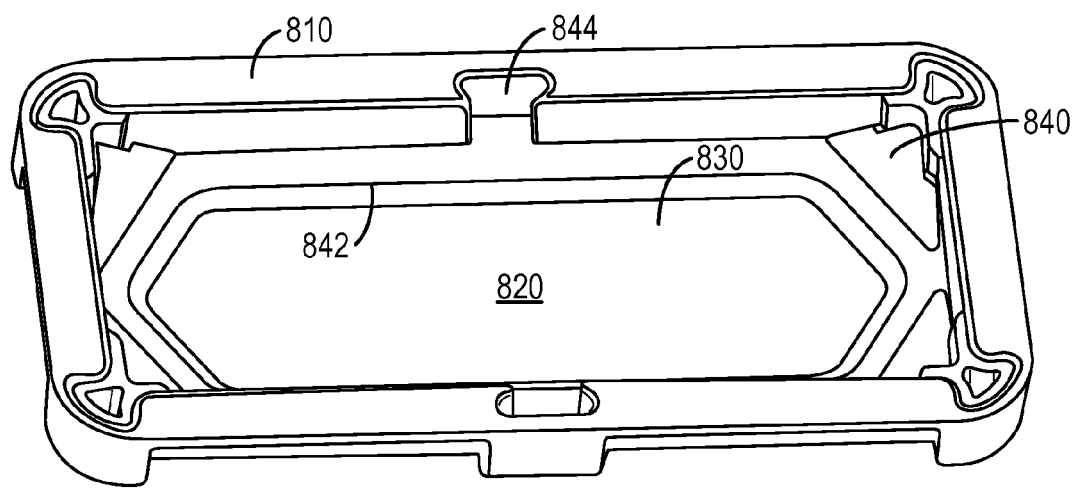
FIG. 8B is a perspective view of the underside of the exemplary embodiment of FIG. 8A with a substrate mounted into the carrier in accordance with the present teachings.

With reference to FIG. 8A, one exemplary embodiment of a slide carrier is depicted. The slide carrier 800 is in the form of a frame 810 configured to surround a substrate (note shown). In various exemplary embodiments, carrier frames in accordance with exemplary embodiments can be made of machined aluminum. Other suitable materials for the carrier frames disclosed herein can include materials that are stiff enough to withstand a force required to compress a sealing mechanism on a heater/sample block without flexing. The frame 810 defines a relatively large opening 830 that is configured to substantially align with a portion of the large surface area of an optically transparent sample substrate when the sample substrate is positioned therein. Surrounding the opening 830, the frame 810 has a stepped profile, the lower portion of which as shown in FIG. 8B is configured to support the sample substrate 820 substantially around a perimeter region of the substrate 820. In various exemplary embodiments, for reasons that will become apparent in the description that follows, the substrate 820 can be received in the frame 810 such that the surface of the substrate 820 facing up in the orientation of FIG. 8B is the surface that carries the sample to be analyzed and/or reacted.

Figure 8C:
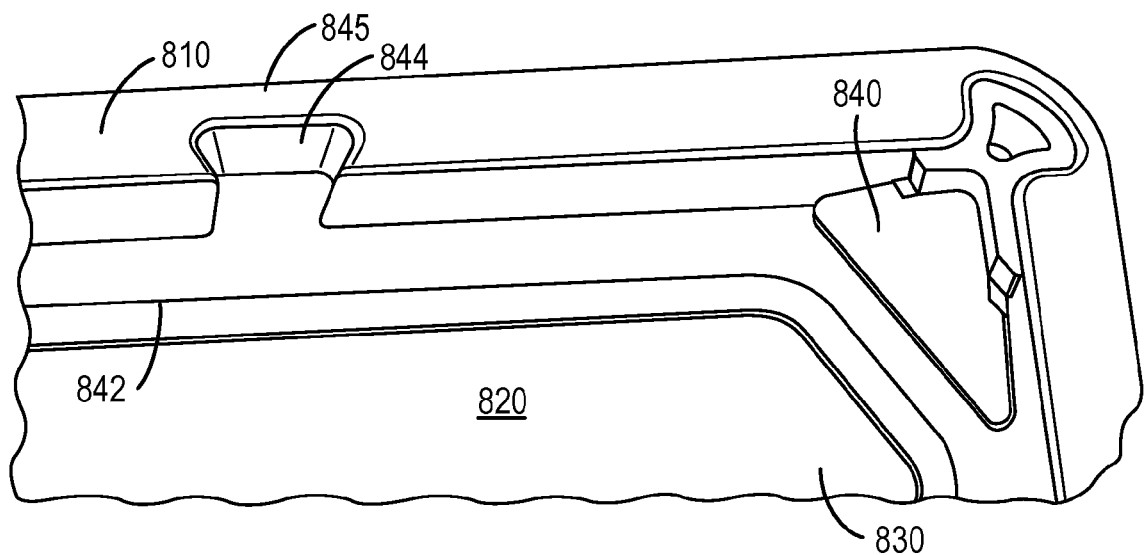
FIG. 8C is a close-up partial view of the exemplary embodiment FIG. 8B.
Figure 8D:
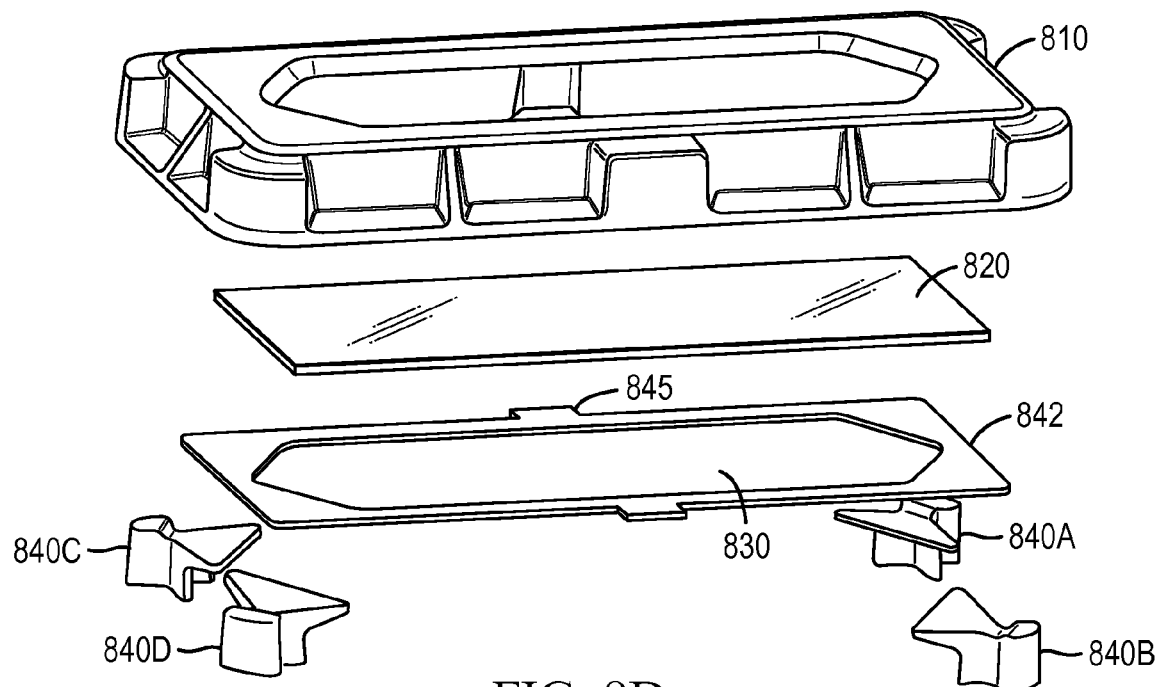
FIG. 8D is a perspective view of an exemplary embodiment of a substrate mounted within a detachable flow cell carrier in accordance with the present teachings.

A view of an exemplary slide carrier 800 in FIG. 8B in an inverted position shows the use of retainer clips 840 at the corners of the slide carrier frame 810 to retain a spacer sheet 842 placed on the underside of substrate 820. Notches 844 in frame 810 serve to retain the narrow edges of spacer sheet 842 eliminating the need for adhesive. As shown in the expanded view of an exemplary slide carrier 800 as illustrated by FIG. 8C, the thickness of the frame 810 can be larger than the thickness of the substrate 820. Retainer clip 840 at each corner of carrier 800 holds spacer sheet 842 in place. FIG. 8D illustrates the assembly of the substrate and retaining components held by a slide carrier. The substrate 820 is in contact with the underside of frame 810 on one surface and with spacer sheet 842 on the opposite, sample surface side. The spacer sheet 842 with notches 845 is held in place by retaining notches 844 within the interior of frame 810 and surrounding opening 830. Retainer clips 840 in each corner of frame 810 secure substrate 820 and spacer sheet 842 to carrier 800. In various exemplary embodiments the substrates can be slides with a microarray of template nucleic acids in proximity to or residing thereon and in respective alignment with the optically transparent regions/opening of the carrier.

In various exemplary embodiments, the retaining mechanisms 840A to 840D can be made of, for example, stainless steel. However, those having skill in the art would recognize other suitable materials from which the retaining mechanisms could be made without departing from the scope of the present teachings.

Figure 9:
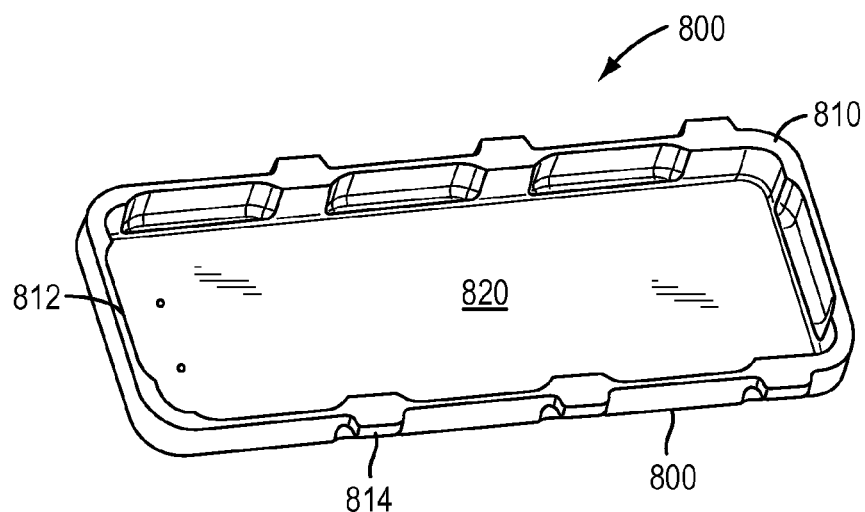
FIG. 9 is a perspective view of the underside of yet another exemplary embodiment of a molded detachable flow cell carrier in accordance with the present teachings.

The underside view of slide carrier 800 as shown in FIG. 9, is yet another exemplary embodiment of a slide carrier which can be formed in a mold. Such a carrier frame 810 can have thin walls 812 to facilitate molding and to reduce heat transfer. The exemplary slide carrier 800 in the form of frame 810 is configured with clip receptacles 814 along the exterior length of the slide carrier 800 for receiving spring-loaded clips (not shown) for attaching the frame 810 securely to the heat block (not shown). In various exemplary embodiments, carrier frames can be made of a plastic, polymer or other materials, natural, synthetic or a combination thereof, know to one of skill in the art to be rigid and thermally stable. Example materials used to form molded slide carrier include, for example, but are not limited to nylon, COP, polycarbonate and so on. Other suitable materials for the carrier frames disclosed herein can include materials that are stiff enough to withstand a force required to compress a sealing mechanism on the heater block without flexing.

Once the substrate 820 for which reaction and/or analysis is desired is positioned and clamped in the carrier 800, the entire carrier 800 with the substrate 820 therein can form a flow cell, as depicted in the exemplary embodiments of FIGS. 10-15.

Figure 10:
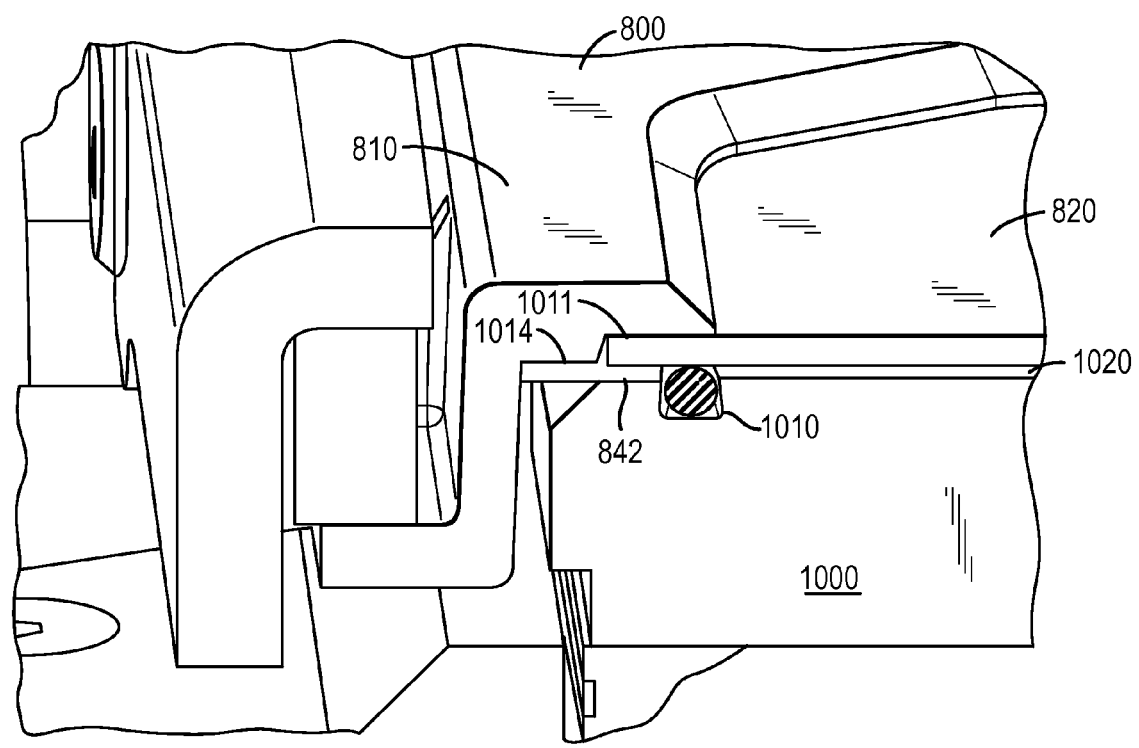
FIG. 10 is a close-up partial sectional view of FIG. 8D resting on a heater block to form exemplary embodiment of a flow cell reaction chamber in accordance with the present teachings.

FIG. 10 illustrates an exemplary flow cell reaction chamber 1020 formed by the joining together of slide carrier 800 with heater block 1000. The stepped profile within the interior surface of frame 810 is also illustrated. The stepped profile provides two regions, the first region 1011 for nesting with the substrate 820 and the second region 1014 for nesting with the heater block 1000. Slide carrier 800 can be made of a metal, e.g., aluminum or a polymer.

In one embodiment, the frame 810 can be configured to envelope the heater block 1000, surrounding it entirely around its perimeter and surface facing away from the heater block 1000. To load the carrier 800, the position of the assembly shown in FIG. 8B is inverted such that the recess shown in FIG. 8B by the frame 810 receives the heater block 1000, causing the surface of the substrate 820 that has sample attached thereon to rest on a sealing mechanism 1010 (e.g., gasket) on the upper surface of the heater block 1000. The sealing mechanism 1010 is configured to engage with a surface 820, such as a slide surface forming a microarray, to create the reaction chamber 1020 into which various substances (e.g., samples, buffers, reagents, lysis solutions, etc.) could be introduced to react with the microarrayed samples (e.g., template nucleic acids) within each formed reaction chamber 1020. The elements 1010 can be any of a variety of mechanisms useful for forming a seal, such as, for example, gaskets, O-rings, and/or other sealing mechanisms with which those having ordinary skill in the art would be familiar.

The sample block 1000 can be made of a material that has a relatively high thermal conductivity. In various exemplary embodiments, the sample block 1000 can be stainless steel, lapped on one side and passivated. Other suitable materials for the sample block 1000 include, but are not limited to, for example, silver, aluminum, copper, and/or various alloys and/or other metals. The block 1000 can be mounted on a frame (not shown).

Various thermal components (some of which are not shown in FIG. 10), such as, for example, a Peltier device, a heat sink, and ducts also are mounted in conjunction with the heater block 1000 to provide thermal cycling within the flow cell reaction chamber 1020. It should be noted that for simplicity the various ports and flow structures used to introduce substances to and remove substances from the flow cell chambers to react with the microarrayed substrates therein are not shown in FIG. 10. Those ordinarily skilled in the art are familiar with various flow control mechanisms, including but not limited to, for example, ports, piping, conduits, valves, and/or other flow control devices (not shown), that can be used to flow various samples, buffers, reagents and/or other substances into and out of the reaction chambers. Those having skill in the art would understand how such flow control mechanisms can be configured and disposed to flow substances into and out of the reaction chambers.

Other components can also be used to provide temperature control and exchange heat with the reaction chamber of the flow cell and various mounting configurations of thermal blocks and substrate surfaces, and are described in more detail in U.S. application Ser. Nos. 11/757,286 and 12/244,701, incorporated by reference herein, and can be used in conjunction with the exemplary embodiments of the present teachings.

Figure 11:
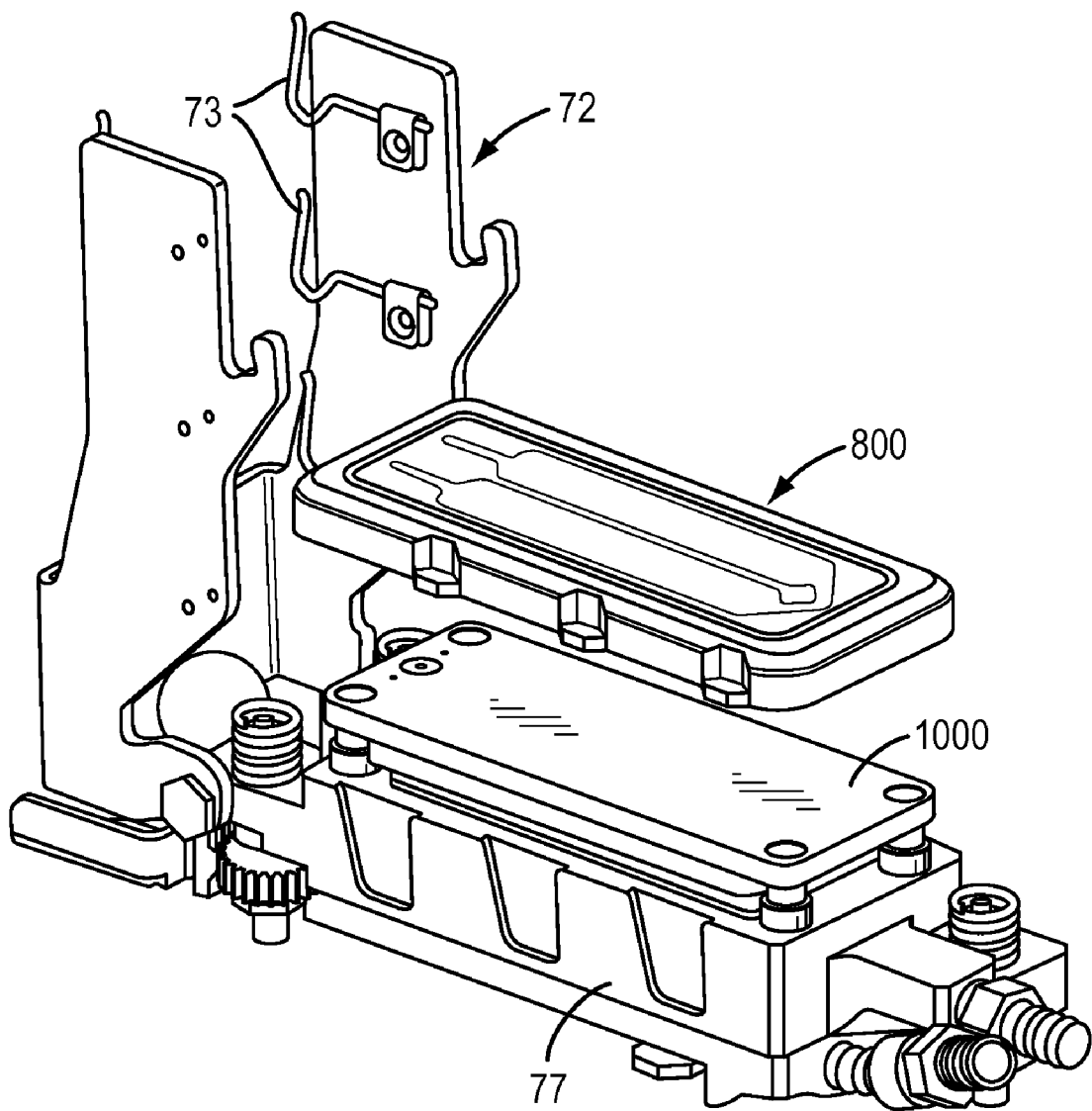
FIG. 11 is a perspective view of the exemplary embodiment of a detachable flow cell carrier of FIG. 7A to be placed upon a heater block and clamped in an immoveable position in accordance with the present teachings.
Figure 12:
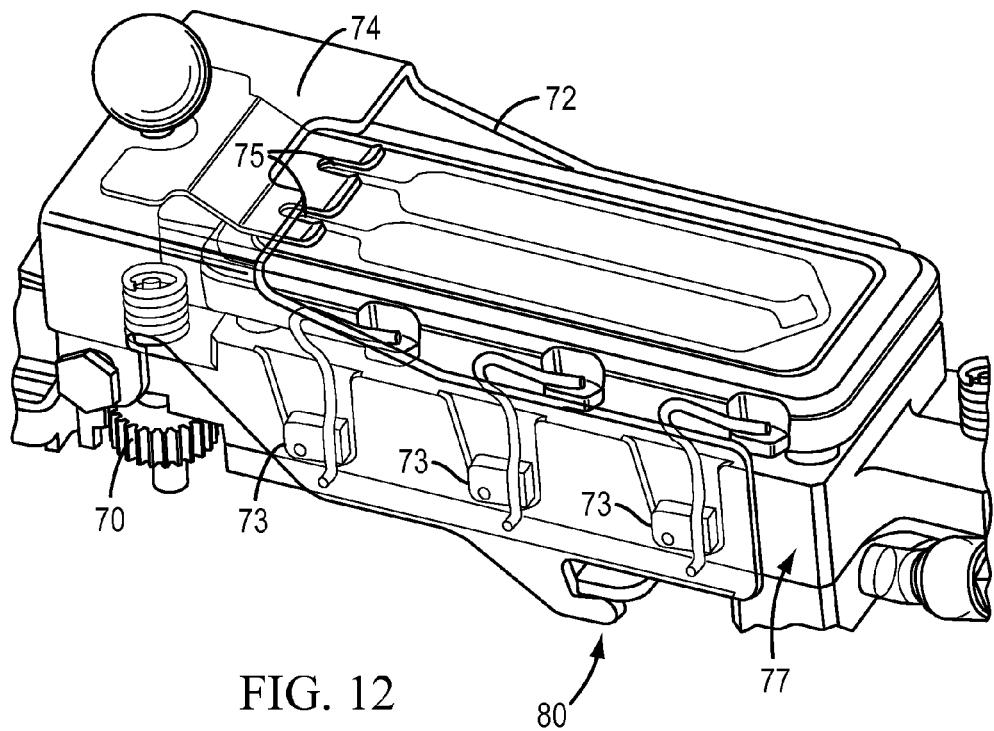
FIG. 12 shows the detachable flow cell carrier of FIG. 11 clamped to the heater block except that the clamping lever is transparent.
Figure 13:
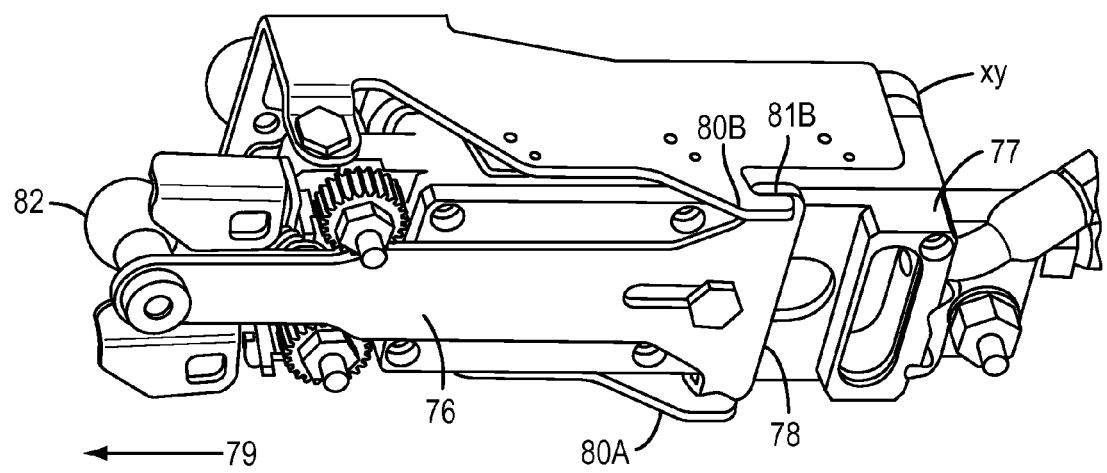
FIG. 13 is a perspective view of the underside of the exemplary embodiment of FIG. 12 in accordance with the present teachings.

FIGS. 11-13 illustrate other exemplary embodiments of a slide carrier 800 and a clamping arm 72 in accordance with the present teachings. The slide carrier of the exemplary embodiment of FIGS. 11-13 is similar to that described above with reference to FIGS. 7A-7B and 8A-8D with modifications to the retaining fingers and clamping surfaces that engage with the clamping arm of the exemplary embodiment of FIGS. 11-13.

Those having skill in the art are familiar with the mounting of flow cells to a vertically positioned translation stage. It should be understood, however, that the flow cells can have orientations other than vertical during reaction and analysis. Those skilled in the art would understand various modifications could be made to provide a flow cell in another orientation without departing from the scope of the present teachings.

By permitting independent access to each flow cell within a multi-flow cell arrangement, various loading and/or unloading steps can take place in one reaction chamber while other reaction chambers undergoing processing and/or imaging steps. Permitting the reactions in flow cell reaction chambers to occur independently of each other also can permit each microarray substrate to be loaded into the flow cell reaction chamber more quickly, thereby hindering drying out of the substrates during loading. Further, in cases where a reaction and/or processing occurring in one flow cell reaction chamber needs to be terminated for whatever reason and sample removed therefrom, the reaction and/or processing in the other flow cell reaction chambers can continue uninterrupted. Moreover, by allowing the plurality of flow cells to be independently accessed and providing them with independent thermal components, reagent inlet and outlet ports, and thermal isolation from each other, processing of two or more differing samples at differing temperature cycles can occur without the temperature variation affecting the focus of the optics and detection equipment. More specifically, changes in temperature of various portions of the flow cell (e.g., metal portions) can cause those portions to expand and/or buckle, which can disturb the focus of the optics. Utilizing independent flow cells that are thermally isolated from each other can permit the flow cells to be maintained at a substantially constant temperature for each processing cycle and thereby minimize the risk of adversely affecting the focusing of the focusing and/or detection optics (for example a microscope).

Various exemplary embodiments of a plurality of flow cells that are independently accessible and that permit a user to form a flow cell reaction chamber for analysis in an incline or horizontal position initially will now be described. Incline angles can be at least 10 degree, at least 30 degrees and up to at least 45 degrees.

FIGS. 11-13 further illustrate an exemplary mechanism for immovably holding a molded slide carrier 800 on the heat block 1000. A dual-sided clamp 72 shown in the open position hinges down over the slide carrier 800 shown elevated above the heat block 1000. Multiple spring-loaded clips 73 attached to the interior of clamp 72 and interlock with carrier 800 to securely hold carrier 800 to the heat block 1000 (covered by carrier 800 and so not visible in FIG. 12). FIG. 12 provides a transparent view of clamp 72. A leaf spring device 74 within the interior of clamp 72 at the upper end of the clamp is shown clamping down over the fluid ports 75 to seal the edges of the flow cell. The clamp 72 is locked closed over carrier 800 by means of a draw bar 76 underneath the heat sink 77 holding heat block assembly 1000. FIG. 13 is a view of the underside of the heat sink 77. Shown is clamp 72 locked down and closed over carrier 800 by interlocking draw bar 76 with mated clamp projection 78 interlocking with projection 80 of clamp 72. Draw bar 76 is shown closed, the open position requiring the bar to move in a horizontal direction (arrow 79), opposite the closed position.

FIGS. 11 and 12 show a detachable flow cell (within slide carrier 800) in a closed and open position, respectively. The flow cell can have a configuration similar to the flow cell 7A described above and is immovably secured to the support frame surrounding heat sink 77. The flow cell 7A can have a heater block 1000 with a sealing mechanism 1020 thereon that ultimately is supported on heat sink 77. The carrier frame 810 can be attached via a hinge 70 (e.g., a leaf-spring hinge), to a clamp 72. In the exemplary embodiment of FIG. 12, the clamp 72 is transparent and can be an opened to remove the carrier, as explained in more detail below. The carrier frame 810 can have a recessed region configured to receive the substrate 820, which because of the detachable configuration of the carrier, can be mounted by a user in a horizontal position as shown in FIG. 11. Small holes 75, the function of which is explained in more detail below, are not obscured by the clamping mechanism 72 when the carrier is mated to the heater block forming the flow cell reaction chamber.

Mounting the carrier 800 and substrate 820 in this manner forms a flow cell reaction chamber 1020 between the substrate 820 and the heater block 1000 into which various substances (e.g., samples, reagents, buffers, etc.) can be introduced for the purpose of reacting with a sample on the substrate 820 and/or performing analysis of the substrate 820. Those ordinarily skilled in the art would understand various flow structures and flow control mechanisms (e.g., ports, conduits, valving, pumps, etc.) that can be used to introduce substances into the reaction chambers of the flow cells described herein; details regarding such flow mechanisms therefore are not provided. Operation and additional details regarding the reaction chamber are described below. Additional description of immovably attaching a slide carrier, forming a flow cell reaction chamber and the clamping mechanisms are described in more detail in U.S. application Ser. Nos. 11/757,286 and 12/244,701, incorporated by reference herein.

As shown in FIGS. 11-13, each flow cell is provided with a closure mechanism, which in various exemplary embodiments can be a lever locks 72. The lever lock can be pivotably mounted to the heat sink 77. As shown in FIG. 11, the lever 72 is provided with a hook-type mechanism 80 on one end thereof configured to respectively engage with a lip 78 on protruding flanges 81A and 81B provided on the lever lock 72 to secure the flow cell in a closed position. The engagement between the lip 78 and the flange 81B is shown in FIG. 13.

FIGS. 11-13 further illustrates an exemplary mechanism for immovably holding the molded slide carrier 800 on the heat block 1000. A dual-sided clamp 72 shown in FIG. 11 the open position hinges down over the slide carrier 800 shown elevated above the heat block 1000. Multiple spring-loaded clips 73 attached to the interior of clamp 72 and interlock with carrier 800 to securely hold carrier 800 to the heat block 1000 (covered by carrier 800 and so not visible in FIG. 12). FIG. 12 provides a transparent view of clamp 72. A leaf spring device 74 within the interior of claim 72 at the upper end of the clamp is shown clamping down over the fluid ports 75 to seal the edges of the flow cell reaction chamber. The clamp 72 is locked closed over carrier frame 810 by means of a draw bar 76 underneath the heat sink 77 holding heat block assembly 1000.

FIG. 13 is a view of the underside of the heat sink 77. Shown is clamp 72 locked down and closed over carrier 800 by interlocking draw bar 76 with mated clamp projection 78 interlocking with projection 80 of clamp 72. Draw bar 76 is shown closed, the open position requiring the bar to move in a horizontal direction (arrow 79), opposite the closed position.

Aside from a detachable flow cell arrangement that permits positioning a substrate in a horizontal position in the flow cell prior to closing the flow cell, it can be desirable to provide an independently accessible multiple (e.g., dual, triple, quadruple, quintuple, etc.) flow cell arrangement removably or permanently mounted to the translation stage that is configured to permit positioning of a substrate by a user prior to performing reactions and/or analysis on the substrate. In one embodiment, two to ten or more flow cells can be either removably mounted or arranged permanently mounted to the translation stage. Such an arrangement can permit loading the substrate and beginning reactions in the flow cells to be accomplished more quickly than in an arrangement wherein the flow cells are loaded in a detached position from the stage. Mounted flow cells can be connected to various reservoirs, pumps, and other flow mechanisms to flow substances for reaction and/or analysis into and out of the flow cell. Also, by securing removable or immovably attaching a flow cell reaction chamber to the stage, it can be possible to achieve better control over the positioning of the substrate and thus to focus the optics and other detection mechanisms more accurately.

In various exemplary embodiments, therefore, a flow cell can be configured to be loaded with a substrate in a horizontal position while the flow cell is mounted to a stage. For example, in accordance with various exemplary embodiments, a user can load a substrate onto the sample block of the flow cell with the flow cell in an open position and, after the substrate is loaded on the sample block, close the flow cell such that the substrate is in a substantially vertical position in the formed flow cell reaction chamber for performing reactions and/or analysis. When utilizing a flow cell arrangement in which a substrate is loaded in a horizontal position, but moved to a vertical position for performing reactions and/or analysis when the flow cell is closed, it is desirable that the flow cell is configured to precisely position the substrate such that accurate imaging and detection of the substrate occurs.

Thus, for example, it may be desirable that the plane of the sample block on which the substrate is mounted and the plane of the substrate surface being imaged is substantially parallel to a focal plane of the imaging optics (e.g., including the various optics and detection elements used to image the substrate or the microscope). Moreover, since in some cases the focal range of the optics may be somewhat limited, placing the substrate in a substantially predictable position when the flow cell is closed can make focusing on the substrate more efficient.

The configuration of the flow cell depicted in FIGS. 7 and 9 is like that of the flow cells 1400A-1400D in FIG. 14 and the flow cell depicted in FIGS. 8 and 10 is like that of the flow cells 1500A-1500D in FIG. 15, described below. It should be understood that the manner in which the substrate carrier 800 is loaded can also be implemented in a flow cell having a configuration like that of flow cells 1600A-1600D illustrated in FIG. 16A-16B. In FIGS. 16A-16B, the flow cell being described is flow cell 1600A; it should be understood that the various parts of the flow cell 1600A applies to the flow cells 1600B-1600D.

Figure 14:
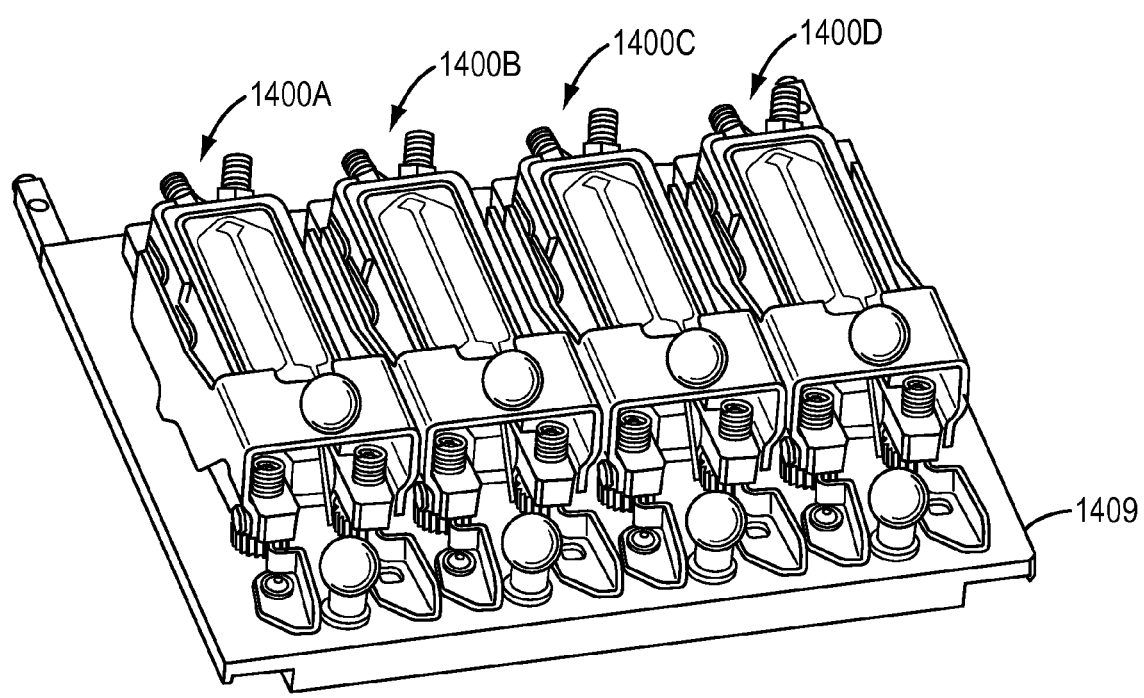
FIG. 14 is a perspective view of an exemplary embodiment of a plurality of detachable flow cell carriers according to FIG. 12 mounted to a translational stage in accordance with the present teachings.
Figure 15:
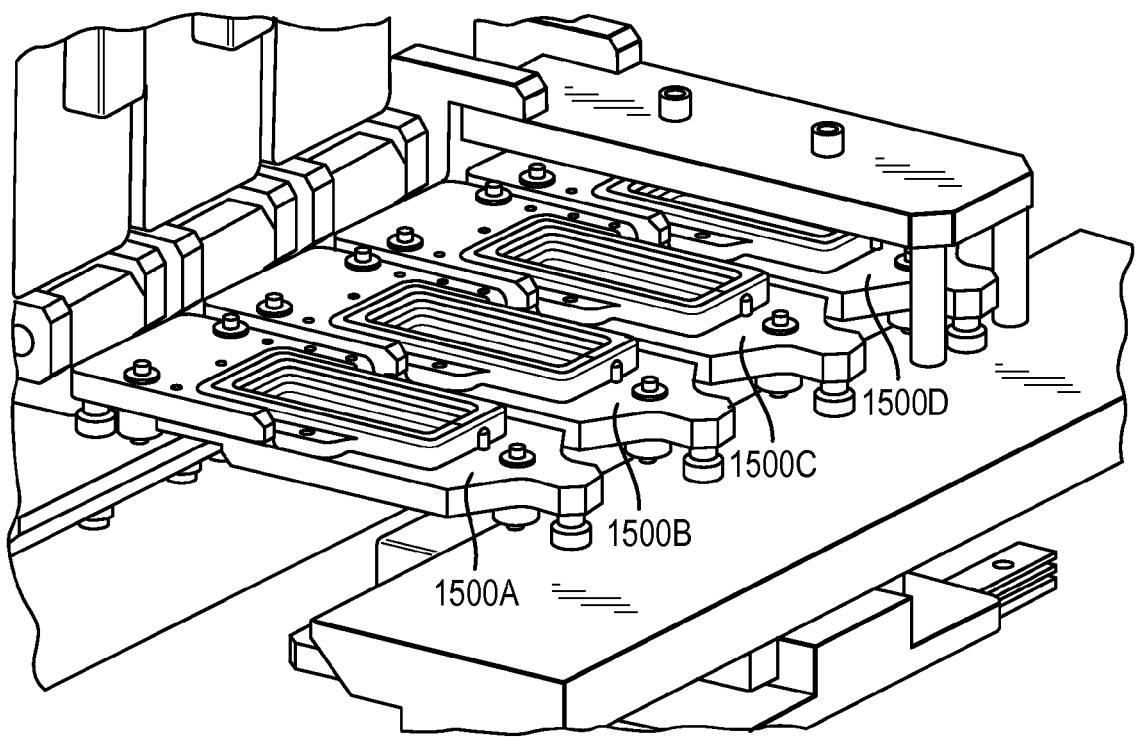
FIG. 15 is a perspective view of an exemplary embodiment of a plurality of detachable flow cell carriers according to FIG. 10 in accordance with the present teachings.
Figure 16A:
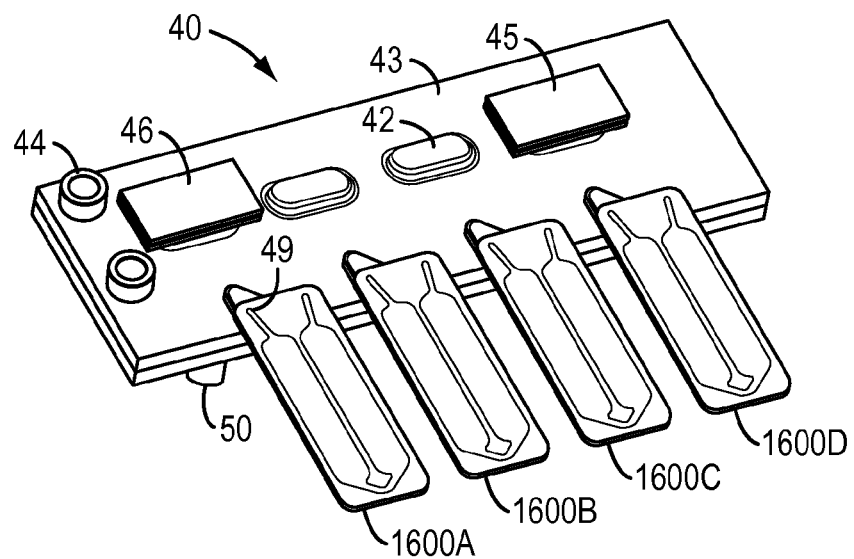
FIG. 16A is a perspective view of an exemplary embodiment of a manifold used to transport aqueous liquids in response to an electrical field and into a plurality of flow cells of FIG. 7A in accordance with the present teachings.
Figure 16B:
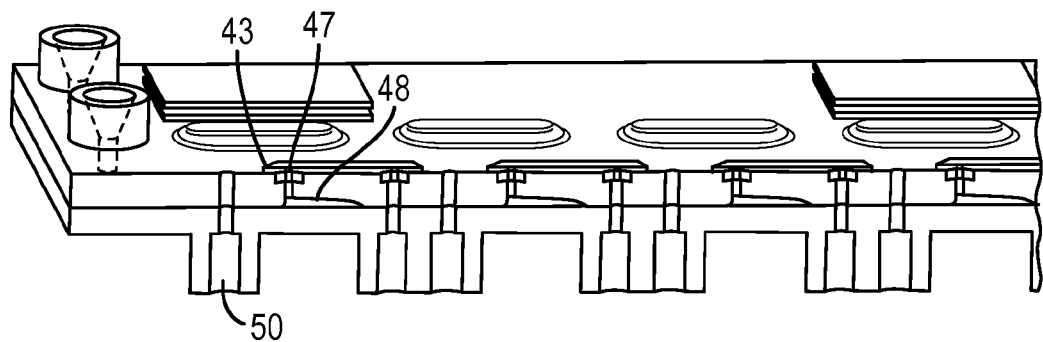
FIG. 16B is a close-up partial sectional view of the exemplary embodiment of FIG. 16A.

A multi-flow cell configurations such as those shown in the exemplary embodiments of FIGS. 14 and 15 permit differing reactions and/or analysis to be taking place at the same time within the different reaction chambers. A multi-flow cell arrangement such as that illustrated in the exemplary embodiments of FIGS. 14 and 15 also can permit one flow cell to be imaged while other process steps such as, for example, loading, sample handling, extension, ligation, and/or cleavage, are being performed in other flow cells. This can maximize utilization of the optical system while increasing throughput. Further, a multi-flow cell arrangement can permit the processing and/or analysis of differing samples to occur.

One exemplary embodiment of an independently accessible multi-flow cell containing biological analysis instrument that permits a user to load a substrate into the flow cells in a horizontal position (e.g., with the large surface area of the substrate substantially parallel to the ground) is depicted in FIG. 14. In that exemplary embodiment, one or more frames, such as frames 1400A to 1400D can be affixed to the stage 1409 and used to achieve appropriate positioning of a substrate being analyzed in a flow cell mounted to the frame when the flow cell is in a closed position, as will be explained in more detail below.

With reference to the exemplary embodiment of FIGS. 14 and 15, a plurality of flow cells, for example, four flow cells, can be secured to a translation stage that is in a horizontal position (e.g., configured to be parallel to the ground) as in FIG. 14 or to individual translation stages also horizontally positioned as in FIG. 15. For further details regarding advantages of having the substrate to be analyzed transportable by means of a sample carrier clamped immovably to a translation stage in conjunction with flow cell instruments, reference is made to WO 2006/084132 and U.S. patent application Ser. No. 12/244,701, incorporated by reference herein.

FIGS. 14, 15 and 16 illustrate exemplary embodiments that permit independent access to each flow cell chamber of a multi-flow cell instrument. Those having ordinary skill in the art would understand, the variety of cooling systems, such as, for example, recirculating chilling fluid-based systems, can be used in combination with the multi-flow cell configurations of FIGS. 14, 15 and 16. Modifications to replace the cooling components, other thermal components, and/or flow control mechanisms for introducing various reagents, sample, buffers, etc. to each flow cell chamber 1400A to 1400D independently would be obvious to those having ordinary skilled in the art and are not described in detail herein.

Those having ordinary skill in the art would understand that the various thermal components depicted in FIG. 14, can be replaced or used in combination with various other thermal components to heat and cool the flow cell reaction chambers. Such thermal components that can be used include, but are not limited to, recirculating cooling liquid systems, heat pipes, evaporative cooling, and various other thermal systems. Ductwork components connecting various thermal components and their connection points in relation to the heating and cooling of the flow cell reaction chambers would be understood by one of ordinary skill in the art and are not discussed further. As mentioned above, the various flow cells described herein in accordance with exemplary embodiments of the present teachings can include various thermal components to provide thermal cycling and/or other temperature regulation of the flow cell. Details regarding various thermal systems and components that can be used in conjunction with the exemplary embodiments of the present teachings as well as ductwork components and connections are further described in U.S. application Ser. Nos. 11/757,286 and 12/244,701, incorporated by reference herein.

In the exemplary configuration of FIG. 16A an electrowetted reagent manifold 40 shuttles reagents between flow cells 1600A-1600D and in and out of temporary reagent reservoir 42 by an array of uniformly or independently controlled electrowetted flow channels 43. Reagents can be introduced into the manifold 40 via ports 44. The manifold 40 can also be fitted with cooling 45 and/or heating 46 reservoirs. Heating can be by Peltier or other mechanisms know to one of ordinary skill in the art. As shown in FIG. 16A and an expanded cross-sectional view in FIG. 16B, reagents can enter a flow cell by way of the flow cell channel 43 in response to an electrical charge and them move through a reagent inlet port 47 connected to a transfer reservoir 48 in response to an electrical charge. Although the electrowetting process is described for flow cell 1600A, the electrowetting process would also apply to flow cells 1600B-1600D. Reagents would enter the flow cell 1600A in response to an electrical charge, for example, via a port 49 connecting the flow cell 1600A to the manifold 40 (as shown in FIG. 16A). Reactions occur within the flow cell 1600A based on the reagent in the flow cell and temperature of the heat block (not shown) and would be separately controlled for each flow cell. Reagents exit the flow cell through port 49 in response to an electrical charge and are either held in the transfer reservoir 48 or travel along the flow cell channel and back to storage reservoir 42, for disposal through a waste port 50 or into an aspirate/wash port 51, each step occurring in response to an electrical charge. The electric field can be conveyed to the manifold in a variety of mechanisms including electrowetting, an electric field, an electrode and/or dielectrophoresis and so on. For further details regarding water-based fluid movement as directed by an electrical field, reference is made to U.S. Pat. No. 7,439,014, incorporated by reference herein.

Those having skill in the art are familiar with the mounting of flow cells to a vertically positioned translation stage. It should be understood, however, that the flow cells can have orientations other than vertical during reaction and analysis. Those skilled in the art would understand various modifications could be made to provide a flow cell in another orientation without departing from the scope of the present teachings.

Although in various exemplary embodiments, the flow cells described herein were described with reference to performing sequencing by synthesis on microarrayed substrates, those having ordinary skill in the art would recognize that the flow cells in accordance with various embodiments of the present teachings can be configured to perform various biological analyses and reaction processes therein, including, but not limited to, for example, nucleic acid analysis methods, such as, for example, sequencing and/or hybridization assays, protein analysis methods, binding assays, screening assays, and/or synthesis, for example, to generate combinatorial libraries, and/or other biological processes and analysis methods. It should also be understood, that any number of flow cells can be provided, with the dual embodiments shown and described herein being exemplary and nonlimiting.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for performing biological sample reactions, the device comprising: a plurality of flow cells comprising at least one port in each flow cell for receiving reaction fluids delivered to at least one chamber of each flow cell; and an electrowetted reagent manifold configured to receive the plurality of flow cells, wherein the electrowetted reagent manifold is configured to deliver and/or remove at least one reaction fluid to at least one chamber of at least one flow cell in response to an electric field generated from an electrode in communication with the manifold.

2. The device of claim 1, wherein the plurality of flow cells are configured to be independently positionable with respect to one another.

3. The device of claim 1, further comprising at least one heater block associated with at least one of the plurality of flow cells.

4. A device for performing biological sample reactions, the device comprising a plurality of independently positionable laminated flow cells; each flow cell further comprising at least two channels comprising an entry port and an exit port wherein at least one reaction fluid is introduced into said flow cells through the entry port and leaves said flow cells through the exit port; and an electro-modified surface in communication with the flow cells, the electro-modified surface configured to deliver and/or remove at least one reaction fluid to at least one chamber of at least one flow cells in response to an electric field generated from an electrode on the electro-modified surface.

5. The device of claim 4, wherein the electro-modified surface is within a common manifold.

6. The device of claim 4, further comprising at least one heater block associated with at least one of the plurality of flow cells.

7. A device for performing biological sample reactions, the device comprising:
a plurality of independently moveable flow cells comprising at least one port in each flow cell for receiving reaction fluids delivered to a chamber of each flow cell, each flow cell further comprising an at least partially transparent portion through which selected optical signals can be transmitted; an electro-mediated reagent delivery system configured to deliver and/or remove at least one reagent fluid to at least one chamber of at least one flow cell by application of an electric field to the reagent fluid and/or a surface in communication with the reagent fluid an optical system configured to detect optical signals transmitted through the at least partially transparent portion of the flow cell; and at least one biological sample contained within the chamber of the flow cell which transmits an optical signal detectable by the optical system.

8. The device of claim 7, wherein at least one of the independently moveable flow cells is positioned such that the optical system can detect optical signals transmitted through the flow cell while another of the at least one independently moveable flow cells is simultaneously positioned apart from the optical system.

9. The device of claim 7, wherein at least one of the independently moveable flow cells is positioned such that the optical system can detect optical signals transmitted through the flow cell while another of the at least one independently moveable flow cells is simultaneously positioned such that it may be loaded with biological sample by a user.

10. The device of claim 7, wherein the plurality of flow cells are mounted to the common manifold.

11. The device of claim 7, wherein the electro-mediated reagent deliver system comprises at least one of the following systems: electrowetting, electrode-mediation or dielectrophoresis-mediation.

12. The device of claim 7, further comprising at least one heater block associated with the plurality of flow cells.

* * * * *